United States Patent
Golobish et al.

(10) Patent No.: US 10,889,665 B2
(45) Date of Patent: Jan. 12, 2021

(54) PROCESS FOR FUNCTIONALIZING A BIOCOMPATIBLE POLYMERIC BEAD, THE FUNCTIONALIZED BEADS, AND THE BEADS PRODUCED THEREBY

(71) Applicant: CytoSorbents, Inc., Monmouth Junction, NJ (US)

(72) Inventors: Thomas Golobish, Monmouth Junction, NJ (US); Tamaz Guliashvili, Monmouth Junction, NJ (US); Vincent Capponi, Monmouth Junction, NJ (US)

(73) Assignee: CYTOSORBENTS, INC., Monmouth Junction, NJ (US)

( * ) Notice: Subject to any disclaimer, the term of this patent is extended or adjusted under 35 U.S.C. 154(b) by 104 days.

(21) Appl. No.: 16/408,977

(22) Filed: May 10, 2019

(65) Prior Publication Data
US 2019/0352437 A1    Nov. 21, 2019

Related U.S. Application Data

(60) Provisional application No. 62/671,665, filed on May 15, 2018.

(51) Int. Cl.
| | | |
|---|---|---|
| *C08F 212/36* | (2006.01) | |
| *C08F 8/08* | (2006.01) | |
| *C08F 212/08* | (2006.01) | |

(52) U.S. Cl.
CPC .............. *C08F 8/08* (2013.01); *C08F 212/08* (2013.01); *C08F 212/36* (2013.01); *C08F 2500/24* (2013.01)

(58) Field of Classification Search
CPC ........ C08F 8/08; C08F 212/08; C08F 212/36; C08F 2500/24; C08F 12/36; C08F 6/005; C08F 6/008; C08J 2300/104; C08J 2201/05; C08J 9/283; C08J 2325/02; B01J 20/267; B01J 20/28083; B01J 20/28004; B01J 20/265; B01J 20/261; B01J 20/3219; B01J 20/321; C12N 11/08
See application file for complete search history.

(56) References Cited

U.S. PATENT DOCUMENTS 4,882,226 A    11/1989   Schutyser et al.

FOREIGN PATENT DOCUMENTS

| EP | 0264984 A1 | 4/1988 |
| WO | 9939823 A1 | 8/1999 |
| WO | 2017205166 A1 | 11/2017 |

*Primary Examiner* — Robert C Boyle
(74) *Attorney, Agent, or Firm* — Abelman, Frayne & Schwab

(57) ABSTRACT

The invention involves functionalizing polymeric beads, such as DVB beads, to add an epoxide or aldehyde group. The resulting beads are useful in various applications.

4 Claims, 1 Drawing Sheet

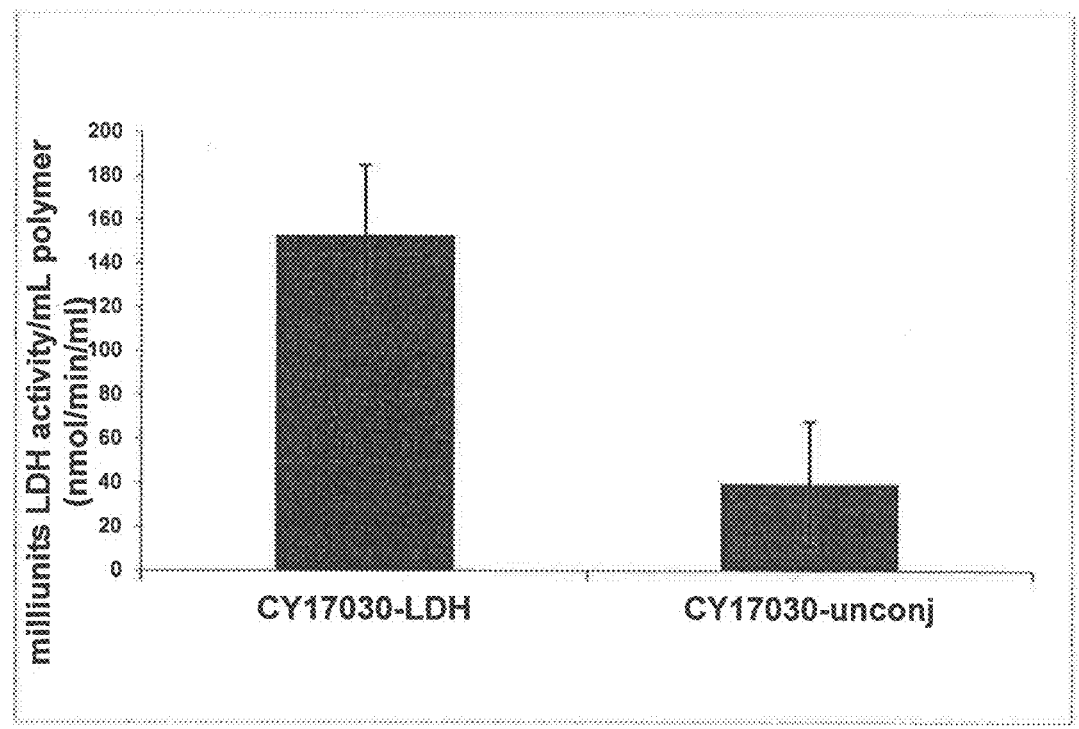
Lactate Dehydrogenase (LDH) activity of epoxy functionalized beads with lactate dehydrogenase via epoxy functionalized surfaces beads. LDH activity was quantified using LDH Assay kit (Sigma).

PROCESS FOR FUNCTIONALIZING A BIOCOMPATIBLE POLYMERIC BEAD, THE FUNCTIONALIZED BEADS, AND THE BEADS PRODUCED THEREBY

PRIORITY

This application claims priority of U.S. provisional application Ser. No. 62/671,665, filed on May 15, 2018, and incorporated by reference in its entirety.

FIELD OF THE INVENTION

The invention relates to processes for functionalizing polymeric beads, especially beads where the base polymer of the bead comprises styrene units, divinylbenzene units, or both. The polymeric beads preferably comprise polystyrene, polydivinylbenzene or poly(styrene-co-divinylbezene) molecules. The polymeric beads are functionalized to add active aldehyde and/or epoxy groups to the surface of the beads, and can then be used, e.g., to attach biological molecules for further use.

BACKGROUND AND PRIOR ART

Polymeric beads are an extremely useful and perhaps essential reagent for fields such as diagnostics, fluid purification, and so forth.

One way in which this polymeric bead is used, is via attachment of a molecule of interest to the bead, which then serves, e.g., as a ligand for a target molecule of interest. Hence, there is ongoing interest in improving the processes by which the beads are prepared. Improvements are sought with respect to safety, cost effectiveness, and purity, for example.

Epoxides and aldehydes are known to be highly reactive compounds which serve as useful molecules for, e.g., attaching biological molecules of interest to a polymeric bead.

Divinyl benzene (DVB) and styrene are common components of polymeric beads. By controlling parameters of the polymerization reactions which result in the beads, one can develop beads with various degrees of porosity and pore size, shape, size, and so forth.

It is known that radical suspension polymerization of divinylbenzene (DVB) never consumes all the vinyl groups of DVB introduced into copolymerization. On average, about 20 to 30% of DVB species fail to serve as crosslinking bridges and remain uninvolved in the resulting network. The presence of a relatively high amount of unreacted vinyl groups is therefore a characteristic feature of DVB beads. It can be expected then that these free vinyl groups are preferably exposed to the surface of the polymer beads and are readily available for chemical modification. The chemical modification of the surface of DVB-copolymers relies on chemical reactions with the surface-exposed vinyl groups and allows conversion to other functional groups. This conversion provides the initial functionality for attachment of a functional linker such as a bioactive ligand.

Various methods of epoxidation been shown to neither be safe nor to be scalable to industrial levels. The invention addresses these issues as it is both scalable and the process is stable at room temperature conditions, ameliorating safety issues.

To elaborate, the invention related to a method for manufacturing a poly(styrene-co-divinylbenzene) or divinylbenzene bead with an epoxide or aldehyde group functionality on its surface. This highly functionalized, stable bead does not require refrigeration. In a preferred embodiment of the invention, the synthesis method involves producing epoxy functional poly(styrene-co-divinylbenzene) or divinylbenzene beads, based on the reaction of residual double bonds of the base material with peroxyacetic acid (peracetic) formed in situ via, e.g., reaction of hydrogen peroxide with acetic acid.

In a preferred embodiment, the invention produces functionalized beads with low residues of organic solvents and unreacted starting materials, therefore enhancing safety. This is preferably accomplished via steam cleaning to yield a product containing a low level of unreacted reagents. The polymeric beads can be nonporous but are preferably porous, with the pores being less than 200 angstroms in diameter to minimize the adsorption of non-specific biomolecules or other unreacted components of their manufacture.

The bead size can range from about 50 microns to about 2.5 cm, preferably from 50-150 microns (μms).

BRIEF DESCRIPTION OF THE FIGURE

FIG. 1 shows the activity of beads prepared according to the invention, with and without a bioactive molecule attached thereto via a functional group attached to the polymeric beads, in accordance with the invention.

DETAILED DESCRIPTION OF THE PREFERRED EMBODIMENTS

Peracetic acid is a strong oxidizing agent, and the reaction of alkene groups with it is also well known. The acid, however, is unstable, and is a severe irritant to the skin, eyes, and respiratory system. Hence, a process which permits the artisan to exploit the oxidative properties of the acid by generating it in situ when needed, is desirable.

The invention involves the in situ generation of peracetic acid in combination with polymeric beads, which are preferably porous and biocompatible, and which present free (unreacted) vinyl groups on their surface. The result is an activated polymeric bead, which presents highly reactive epoxides on its surface. In some embodiments, these epoxides can be reacted to form aldehydes, which are also reactive.

The following examples are intended to be illustrative and not limiting.

Example 1

This example describes the synthesis of dry polymer beads, having a size distribution of 50-150 μm diameter.

The beads were prepared using well known suspension polymerization methods. To elaborate, a solution of polyvinyl alcohol in deionized water was used as a dispersant, divinylbenzene ("DVB") was the monomer, and toluene as the porogen. Operation of the suspension polymerization method resulted in production of polymer beads, having a size distribution of 50-150 μm diameter. The beads were epoxidated using a solution of hydrogen peroxide (30% in water), and a 99% solution of acetic acid.

The reaction of hydrogen peroxide and acetic acid leads to the formation of peroxyacetic acid, as an epoxidizing agent.

Example 2

Polyvinyl alcohol (3.0 g) was dissolved in 500 ml deionized water, to form an aqueous phase. An organic phase was formed by combining 160 g of a DVB solution (63% pure DVB isomer content), 240 g of 99% toluene, and 98% benzoyl peroxide as the radical polymerization initiator. A 1 liter jacketed reactor, equipped with a mechanical agitator, was charged with the aqueous phase referred to supra, and heated to 80° C. at 300 rpm. The organic phase was added and the reaction was allowed to run for 16 hours, at 80° C. After the end of the reaction, the beads produced were washed, three times, in 500 ml deionized water, and steam stripped for 8 hours to remove any residual starting reagents. Beads were sieved, and dried at 90° C., for 24 hours. The yield was 42 g/105 ml dry beads, having diameters over a range of 50-150 µm.

Example 3

In this Example, 41 g of the polymer produced in Example 1, supra, was charged into a 1 liter glass reactor equipped with a TEFLON® coated agitator. A mixture of 200 ml acetic acid, and 75 ml of a 30% aqueous solution of $H_2O_2$ were added. The mixture was heated to 50° C., at 100 rpm, and the reaction was allowed to run for 24 hours. The product was yellowish, polymer beads. These were washed in aliquots of deionized water until the pH of the effluent was about 5.5. The washed beads were dried at 80° C., until the weight of the product remained constant. The yield of dry beads was about 43.5 g.

Example 4

This Example describes the attachment of lactate dehydrogenase to the polymer beads of the invention.

A sample (2 g) of the beads synthesized in Examples 1 and 3 was wetted in 70% isopropanol and then washed, four times, with 50 ml of distilled deionized water. LDH was dissolved in a coupling buffer (0.1M $Na_2CO_3$, pH 9.0) and then reacted with the epoxy functionalized beads described supra, for 16 hours at room temperature, with end over end agitation. Any unreacted epoxy groups in the now functionalized beads were blocked with 1M ethanolamine, at pH 8, for 4 hours at room temperature, also with end over end rocking. The functionalized beads were washed, four times, alternating a wash with 0.1 M acetate buffer containing 0.5 M NaCl (pH 4), with a wash with 0.1 M Tris-HCl buffer containing 0.5 M NaCl, at pH 8.0. Following the four washes, beads were suspended in phosphate saline buffer, and stored at 4° C. until used.

FIG. 1 shows the results of comparative tests to determine LDH activity, using a standard, commercially available LDH activity assay. The samples were conjugated beads, in accordance with this example, and unconjugated beads prepared via Example 1 or 3. Attachment of LDH to the epoxy activated beads shows that the beads can be used in the context of attaching any biological molecule of interest thereto. Polymeric beads having biological materials immobilized therein are well known in the art and their uses need not be elaborated herein.

Once the porous, polymeric beads are activated to present epoxide group on their surface, they can be treated to convert the epoxy group to an aldehyde group. Various methods for accomplishing this are available including, but not being limited to, hydrolysis of epoxide groups, promoted by either acid or base to form benzylic 1,2 diol. The benzylic 1,2 diol is then oxidized directly, at room temperature, with a strong oxidizing agent, such as $NaIO_4$. The result is benzaldehyde functionality.

The polymeric beads used in the instant invention may have a biocompatible and hemocompatible exterior surface coatings but this is not absolutely necessary. Certain of these coatings are covalently bound to the polymeric beads by free-radical grafting. The free-radical grafting may occur, for example, during the transformation of the monomer droplets into polymeric beads. The dispersant which coats and stabilizes the monomer droplets becomes covalently bound to the droplet surface as the monomers within the droplets polymerize and are converted into polymers. Biocompatible and hemocompatible exterior surface coatings can be covalently grafted onto the preformed polymer beads if the dispersant used in the suspension polymerization is not one that imparts biocompatibility or hemocompatibility. Grafting of biocompatible and hemocompatible coatings onto preformed polymer beads is carried out by activating free-radical initiators in the presence of either the monomers or low molecular weight oligomers of the polymers that impart biocompatibility or hemocompatibility to the surface coating.

A "biocompatible" material is defined as any natural or synthetic substance/combination of substances (other than drugs) which may be employed for any length of time as a whole or part of a system, to treat, augment, or replace any tissue, organ or function of the body. The polymeric beads of the present invention are preferably non-toxic.

In some embodiments, the polymer has a preferential pore structure such that pore size is below 200 Å thus allowing efficient steam cleaning to reduce residual organics while still minimizing nonspecific binding of proteins.

Some preferred polymers are coated polymers comprising at least one crosslinking agent and at least one dispersing agent. Suitable dispersing agents include hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly(diethylaminoethyl acrylate), poly(vinyl alcohol), poly(N-vinylpyrrolidinone), salts of poly(methacrylic acid), and salts of poly(acrylic acid) and mixtures thereof.

Suitable crosslinking agents include divinylbenzene, trivinylbenzene, divinylnaphthalene, trivinylcyclohexane, divinylsulfone and mixtures thereof. Preferably, the polymer is developed simultaneously with the formation of the coating, such that the dispersing agent gets chemically bound to the surface of the polymer.

Preferred polymers include those derived from one or more monomers selected from divnylbenzene and ethylvinylbezene, styrene and mixtures thereof.

Some preferred polymers are polysaccharide based polymers. Suitable polymers include cross-linked dextran gels such as Sephadex®.

Certain preferred polymers are porous highly crosslinked styrene or divinylbenzene copolymer. Other of these polymers are a hypercrosslinked polystyrene produced from crosslinked styrene copolymers by an extensive chloromethylation and a subsequent post-crosslinking by treating with a Friedel-Crafts catalyst in a swollen state.

Some polymers useful in the practice of the invention are hydrophilic self wetting polymers that can be utilized as dry powder containing hydrophilic functional groups such as, amines, hydroxyl, sulfonate, and carboxyl groups.

Certain polymers useful in the invention are polymers prepared from the polymerizable monomers of styrene, divinylbenzene, ethylvinylbenzene, and the acrylate and methacrylate monomers such as those listed below by manufacturer. Rohm and Haas Company, (now part of Dow Chemical Company): (i) macroporous polymeric sorbents such as Amberlite™ XAD-1, Amberlite™ XAD-2, Amberlite™ XAD-4, Amberlite™ XAD-7, Amberlite™ XAD-7HP, Amberlite™ XAD-8, Amberlite™ XAD-16, Amberlite™ XAD-16 HP, Amberlite™ XAD-18, Amberlite™ XAD-200, Amberlite™ XAD-1180, Amberlite™ XAD-2000, Amberlite™ XAD-2005, Amberlite™ XAD-2010, Amberlite™ XAD-761, and Amberlite™ XE-305, and chromatographic grade sorbents such as Amberchrom™ CO 71,s,m,c, Amberchrom™ CG 161,s,m,c, Amberchrom™ CG 300,s,m,c, and Amberchrom™ CG 1000,s,m,c. Dow Chemical Company: Dowex® Optipore™ L-493, Dowex® Optipore™ V-493, Dowex® Optipore™ V-502, Dowex® Optipore™ L-285, Dowex® Optipore™ L-323, and Dowex® Optipore™ V-503. Lanxess (formerly Bayer and Sybron): Lewatit® VPOC 1064 MD PH, Lewatit® VPOC 1163, Lewatit® OC EP 63, Lewatit® S 6328A, Lewatit® OC 1066, and Lewatit® 60/150 MIBK. Mitsubishi Chemical Corporation: Diaion® HP 10, Diaion® HP 20, Diaion® HP 21, Diaion® HP 30, Diaion® HP 40, Diaion® HP 50, Diaion® SP70, Diaion® SP 205, Diaion® SP 206, Diaion® SP 207, Diaion® SP 700, Diaion® SP 800, Diaion® SP 825, Diaion® SP 850, Diaion® SP 875, Diaion® HP 1MG, Diaion® HP 2MG, Diaion® CHP 55A, Diaion® CHP 55Y, Diaion® CHP 20A, Diaion® CHP 20Y, Diaion® CHP 2MGY, Diaion® CHP 20P, Diaion® HP 20SS, Diaion® SP 20SS, and Diaion® SP 207SS. Purolite Company: Purosorb™ AP 250 and Purosorb™ AP 400.

Other features of the invention will be clear to the skilled artisan and need not be reiterated here.

The terms and expression which have been employed are used as terms of description and not of limitation, and there is no intention in the use of such terms and expression of excluding any equivalents of the features shown and described or portions thereof, it being recognized that various modifications are possible within the scope of the invention.

The invention claimed is:

1. A process for making a polymeric bead having an epoxide group with a biological molecule attached thereto on its surface, said polymeric beads comprising pores having an average diameter of less than 200 Angstroms, comprising simultaneously contacting a polymeric bead which comprises monomeric divinylbenzene and has pores having an average diameter of less than 200 Angstroms with acetic acid and hydrogen peroxide to form an epoxide group on the surface of said polymeric beads, and attaching a biological molecule to said epoxide group.

2. The process of claim 1, further comprising reacting said epoxide group under hydrolysis and oxidation conditions, to form an aldehyde.

3. The process of claim 1, wherein said polymeric beads have a size distribution of 50-150 µm diameter.

4. The process of claim 1, further comprising steam stripping said polymeric beads to remove any unreacted divinylbenzene therefrom.

* * * * *